US005571093A

United States Patent [19]

Cruz et al.

[11] Patent Number: 5,571,093
[45] Date of Patent: Nov. 5, 1996

[54] MULTIPLE-LUMEN CATHETER

[76] Inventors: Cosme Cruz, 253 Lewiston, Grosse Pointe Farms, Mich. 48236; Richard W. Dow, Rte. 1, Box 12A, Sharon, Vt. 05065; David G. Quinn, 21860 W. Washington St., Grayslake, Ill. 60030

[21] Appl. No.: 310,237

[22] Filed: Sep. 21, 1994

[51] Int. Cl.$^6$ .................... A61M 25/00; A61M 31/00
[52] U.S. Cl. .................... 604/270; 604/39; 604/264; 604/280; 604/283
[58] Field of Search .................... 604/39, 43, 54, 604/264, 266, 268, 270, 275, 280–282, 283

[56] References Cited

U.S. PATENT DOCUMENTS

| | | |
|---|---|---|
| 4,594,074 | 6/1986 | Andersen et al. . |
| 5,053,004 | 10/1991 | Markel et al. . |
| 5,078,701 | 1/1992 | Grassi et al. ............................ 604/270 |
| 5,117,822 | 6/1992 | Laghi ........................................ 604/43 |
| 5,171,216 | 12/1992 | Dease et al. . |
| 5,190,520 | 3/1993 | Fenton, Jr. et al. . |
| 5,209,723 | 5/1993 | Twardowski et al. . |
| 5,221,256 | 6/1993 | Mahurkar ................................ 604/280 |
| 5,320,599 | 6/1994 | Griep et al. ............................ 604/43 |
| 5,348,536 | 9/1994 | Young et al. ........................... 604/280 |

*Primary Examiner*—John D. Yasko
*Assistant Examiner*—Laird J. Knights
*Attorney, Agent, or Firm*—Brinks Hofer Gilson & Lione

[57] ABSTRACT

A multiple-lumen catheter is disclosed that includes a catheter tube having a generally elongate cylindrical body having an axial passageway extending the length thereof. A septum extends across the interior of the body and along the length thereof in order to divide the body into first and second lumens. A bolus extends from a distal end of the body. The bolus has a passage section including an axial passage portion and a radial passage portion. The axial passage portion is in fluid communication with the first and second lumens. The radial passage portion includes a single port through the side of the bolus whereby the first and second lumens are in fluid communication with the port. According to another form of the invention, the radial passage includes a first port and a second port therein.

20 Claims, 4 Drawing Sheets

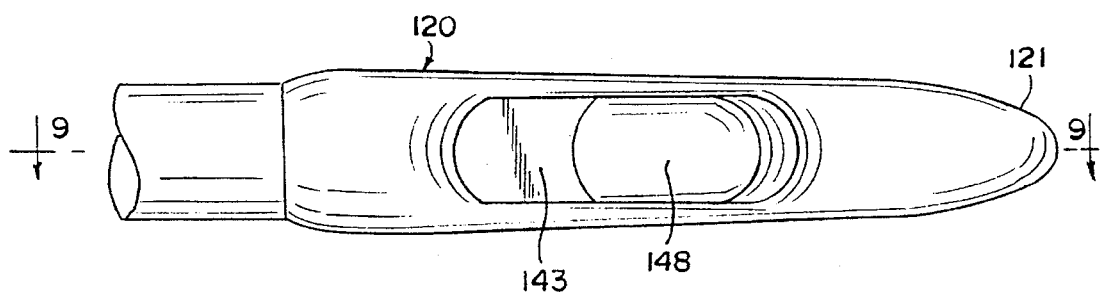
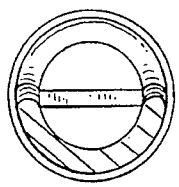
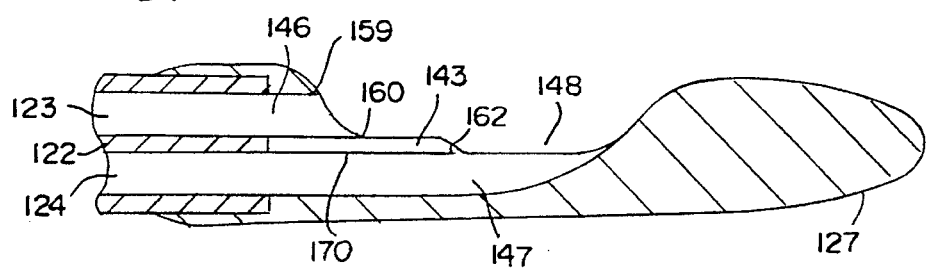
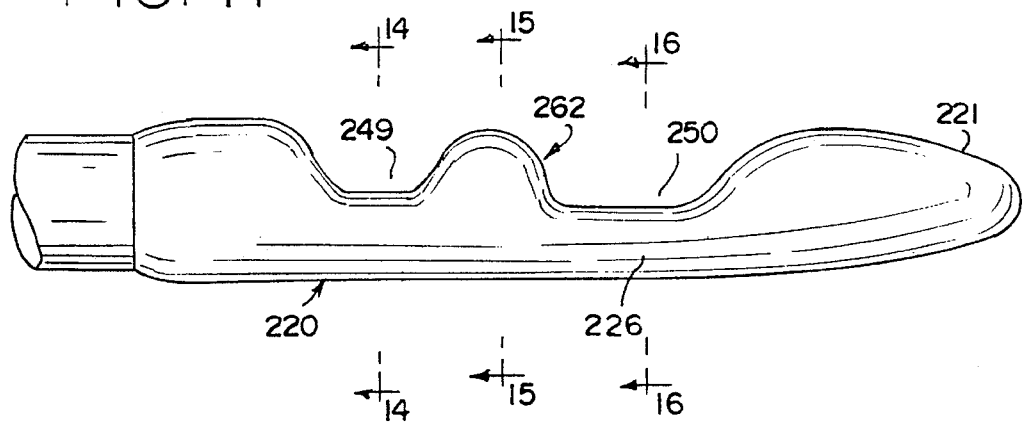

MULTIPLE-LUMEN CATHETER

FIELD OF THE INVENTION

The present invention relates generally to multiple-lumen catheters for use in medical applications where at least two separate fluid flow paths are necessary for the treatment of a patient. More particularly, this invention concerns the distal end of a multiple-lumen catheter which contains an opening for fluid egress and/or ingress.

BACKGROUND OF THE INVENTION

Various medical procedures require the use of a catheter that has at least two separate fluid flow paths or lumens. Catheters having multiple lumens are important because they reduce the number of tubes that must be placed through a patient's skin. One example of the use of a multiple-lumen catheter is in the extracorporeal treatment of blood, as in hemodialysis. During hemodialysis, two separate paths are necessary for the flow of blood. Specifically, one lumen accommodates blood flow from the patient for the treatment of the blood to remove various toxins. The other lumen accommodates the return flow of treated blood to the patient. A further example of the use of a multiple-lumen catheter is the delivery of incompatible medications and/or intravenous fluids.

Several multiple-lumen catheters are known for these purposes. One example of a hemodialysis catheter is shown in U.S. Pat. No. 4,808,155 (the '155 patent) issued to Mahurkar. The catheter shown in the '155 patent has two separate ports, i.e., an infusion port and a withdrawal port, opening from an infusion lumen and a withdrawal lumen. As shown in the '155 patent, the infusion lumen extends the entire length of the catheter and terminates at a flat distal end. The withdrawal lumen is substantially shorter than the infusion lumen and terminates at a point proximal to the distal end of the catheter. As explained in the '155 patent, the separation of the withdrawal port and the infusion port generally prevents mixing of untreated blood initially drawn into the catheter with treated blood being returned to the patient.

However, several disadvantages result from the placement of the infusion port on the distal end of the catheter as shown in the '155 patent. First, the ports may be partially or totally occluded by a buildup of blood components (fibrin) or when the ports press up against the vessel wall. This situation drastically reduces the effectiveness of the treatment. Second, as fluid exits from the infusion port, the catheter is subject to whipping (a quick back and forth movement inside the vein of a patient). Because whipping causes the catheter to continually batter the inside wall of the vein, the vein will be damaged. In addition, whipping may cause clots to form around the outside surface of the catheter tip. These clots can obstruct blood flow through the vessel. They may also become dislodged, creating a free-floating thrombus in the circulatory system. These fibrin deposits are generated by the endothelium of the vessel wall as an inflammatory reaction to the irritation of the catheter whipping. Clot formation and stricture of blood vessels are common complications associated with the implantation of these catheters. Accordingly, there exists a need for a catheter capable of overcoming the above-referenced problems while avoiding the mixing of fluids from the two lumens.

SUMMARY OF THE INVENTION

A primary object of the present invention is to provide an improved bolus for a multiple-lumen catheter tube which minimizes "whipping" of the catheter during all modes of operation and also prevents the mixing of fluids from the separate lumens.

A further object is to provide a multiple-lumen catheter having a bolus which generally prevents the formation of clots in the vein of a patient.

The foregoing and other objects are realized in accordance with the present invention by providing a catheter and a bolus for use in the delivery or withdrawal and delivery of fluids to a patient. The catheter includes a tube comprising a generally elongate cylindrical body having an axial passageway extending the length thereof. A septum extends across the interior of the tube body and along the length thereof in order to divide the body into first and second lumens. A bolus extends from a distal end of the tube body.

According to a first form of the invention, the bolus has a tube connector section at one end, a nose section at the other end and a passage section between the connector section and the nose section. The passage section has an axial passage portion adjacent the connector section and a radial passage portion adjacent the nose section. The axial passage portion is in fluid communication with the first and second lumens. The radial passage portion forms a single port through the side of the bolus with the first and second lumens in fluid communication with the port.

According to another form of the invention, the radial passage portion has a longitudinal cross-section along the septum forming a first portion and a second portion. A first port and a second port are located substantially within the first portion of the radial passage portion. Wherein, the first port and the second port are in fluid communication with the first and second lumens respectively.

BRIEF DESCRIPTION OF THE DRAWINGS

The invention, including its construction and method of operation, is illustrated more or less diagrammatically in the drawings, in which:

FIG. 8 is a top plan view of the bolus seen in FIG. 7;

FIG. 9 is a longitudinal sectional view taken along line 9—9 of FIG. 8;

FIG. 10 is a transverse sectional view taken along line 10—10 of FIG. 7;

FIG. 11 is an illustration of a side view of a bolus embodying a third form of the invention;

DESCRIPTION OF THE PREFERRED EMBODIMENTS

The preferred embodiments are described here in the context of catheters, generally. The principles of the invention apply equally well to all types of catheters, including Foley catheters, urethral catheters and catheters for use in a wide range of diverse applications including hemodialysis procedures and many others.

Figure 1:
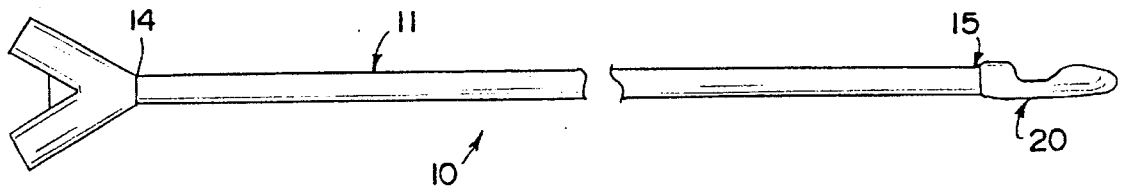
FIG. 1 is an illustration of a first form of a multiple-lumen catheter of the present invention.

Referring now to the drawings, and particularly to FIG. 1, a catheter having a bolus according to a first form of the invention is seen generally at 10. The catheter 10 includes a cylindrical tube 11 which is preferably fabricated from a resilient, biocompatible plastic such as polyurethane. Although other plastics, including polyvinyl chloride, may be used, the properties of polyurethane are such that it can be fabricated with a maximum inside tube diameter and a minimum tube wall thickness. Preferably, an aromatic polyurethane should be used although an aliphatic polyurethane may also be used. Furthermore, thermoset materials such as silicone may also be used.

The tube 11 extends between a proximal end 14, which may be connected to various medical devices required for drug delivery, or as required in hemodialysis, and a terminal or distal end 15. As shown in FIG. 1, the proximal end 14 carries a "Y" connector in order to provide separate access to the below-described lumens found in the tube 11.

The tube 11 may include a radiopaque stripe 16 to facilitate location of the bolus 20, shown seated in the terminal or distal end 15 of the tube 11, inside the vein of a patient by fluoroscope or X-ray. The stripe 16 is uniformly placed along the entire length of the tube 11 in order to provide a reference for the proper orientation of the bolus 20 when the catheter 10 is being implanted and/or is in use. Accordingly, the bolus 20 and more specifically, a port located therein, may be oriented in the vein of a patient away from the wall of the vein to prevent occlusion of the port by contact with the vein wall.

The catheter 10 may also be formed entirely from a radiopaque material. Furthermore, rather than orient the bolus 20 through the use of a radiopaque stripe, a printed marking identifying the position of the bolus 20 may be placed on the tube 11 and/or the "Y" connector.

Referring to FIGS. 2–6, the bolus 20 and its connection to the terminal end 15 of the catheter tube 11 are shown in greater detail. The bolus 20 has a generally tubular-shaped body 21 fabricated from a flexible polyurethane material.

The dimensions of the body 21 vary with the size of the catheter tube in use. Catheter tubes are specified within a standard series of sizes known as "French" sizes. French (FR) sizes designate tubes by their outside diameter. The smallest designation is 3 FR, which has an outside diameter of 1 mm or 0.039". The catheter tube 11 which is utilized in describing the first form of the present invention is a 13 FR tube and is formed from polyurethane. The catheter tube 11 has an outside diameter of 0.170" and an inside diameter of 0.130".

Figure 4:
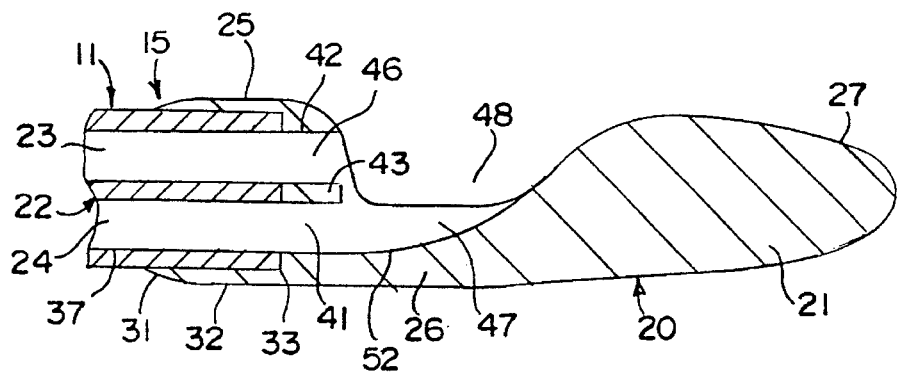
FIG. 4 is a longitudinal sectional view taken along line 4—4 of FIG. 3.
Figure 5:
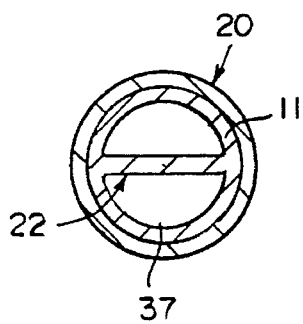
FIG. 5 is a transverse sectional view taken along line 5—5 of FIG. 2.
Figure 6:
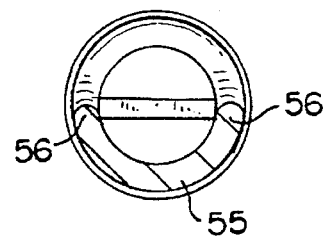
FIG. 6 is a transverse sectional view taken along line 6—6 of FIG. 2.
Figure 7:
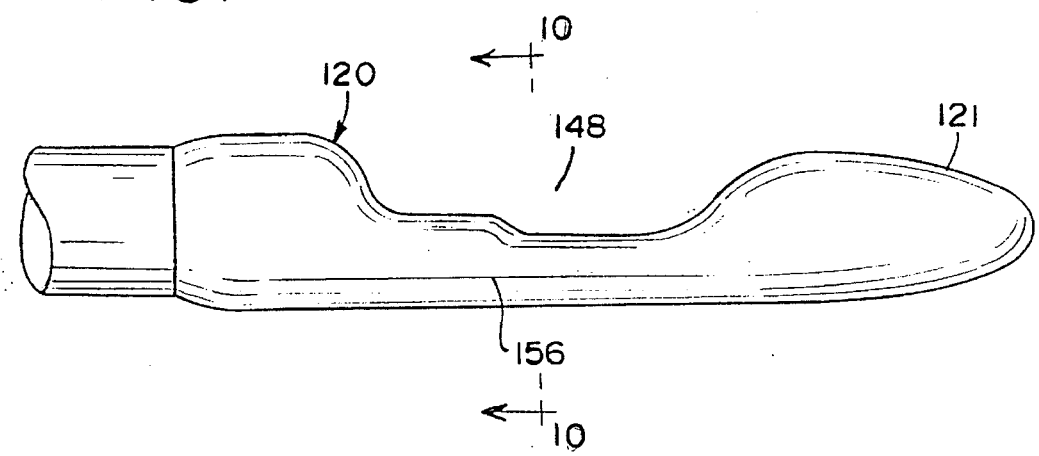
FIG. 7 is an illustration of a side view of a bolus embodying a second form of the invention.
Figure 12:
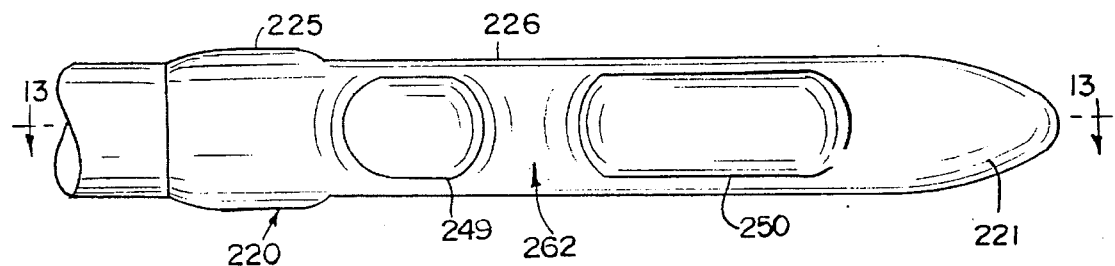
FIG. 12 is top plan view of the bolus seen in FIG. 11.
Figure 13:
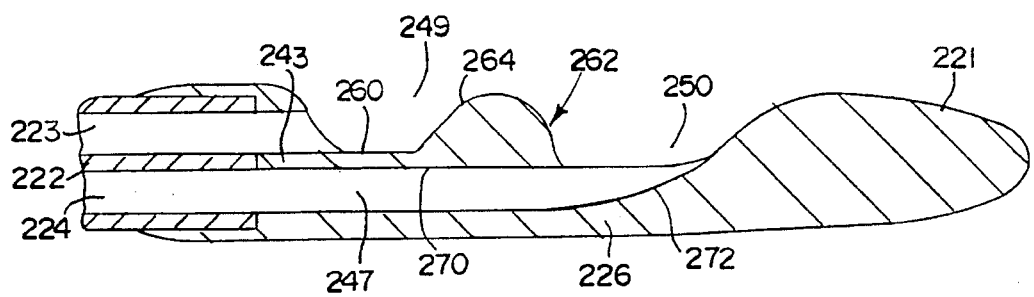
FIG. 13 is a longitudinal sectional view taken along line 13—13 of FIG. 12.
Figure 14:
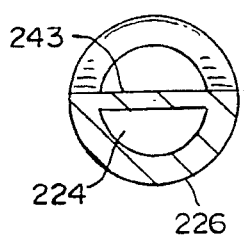
FIG. 14 is a transverse sectional view taken along line 14—14 of FIG. 11.
Figure 15:
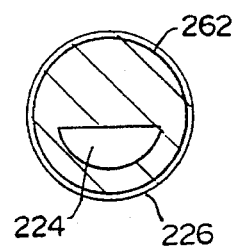
FIG. 15 is a transverse sectional view taken along line 15—15 of FIG. 11.
Figure 16:
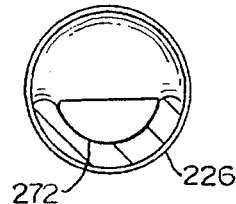
FIG. 16 is a transverse sectional view taken along line 16—16 of FIG. 11.

As best seen in FIGS. 4–6, a septum 22 extends diametrically across and axially along the inside of the body of the tube 11. The septum 22 divides the inside of the body of the tube 11 into a first lumen 23 and a second lumen 24. The first and second lumens 23, 24 have a generally D-shaped cross-section. Preferably, the septum 22 has a thickness of 0.020".

The body 21 of the bolus 20 is formed unitarily, by injection molding and has an overall length of 0.810" in this form. The bolus 20 comprises three distinct body sections. These sections are the tube glue-area section 25, the flow passage section 26 and the bullet-shaped nose section 27.

As best seen in FIG. 4, the terminal end 15 of the tube 11 connects to the bolus 20 by seating in a cylindrical bore 31 formed axially into the proximal end 32 of the body 21. The cylindrical bore 31 extends 0.150" axially into the body 21, where it terminates in a shoulder 33. The axial length of the cylindrical bore 31 forms the tube glue-area section 25 of the body 21. Because the glue-area section must accommodate the tube 11, the outer diameter of this section is slightly larger than the diameter of the tube 11. In this embodiment, the outside diameter of the glue-area section 25 is 0.200".

Figure 2:
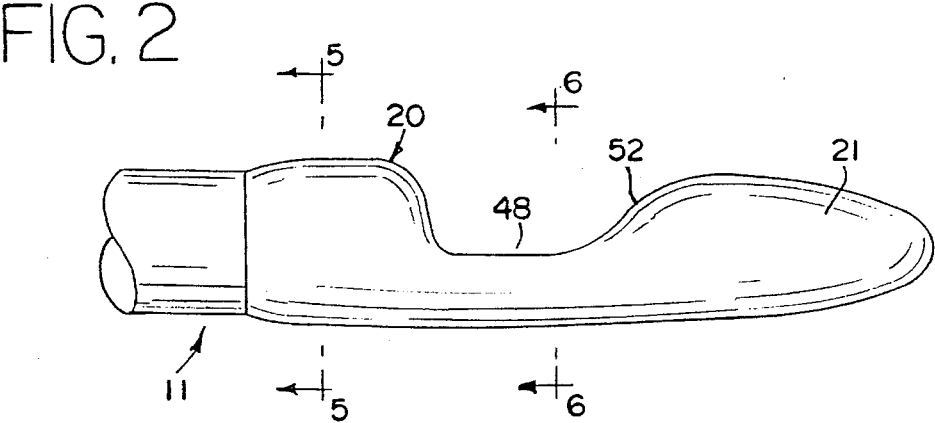
FIG. 2 is an enlarged side view of the bolus end of the catheter seen in FIG. 1, showing the bolus connected to the catheter tube.
Figure 3:
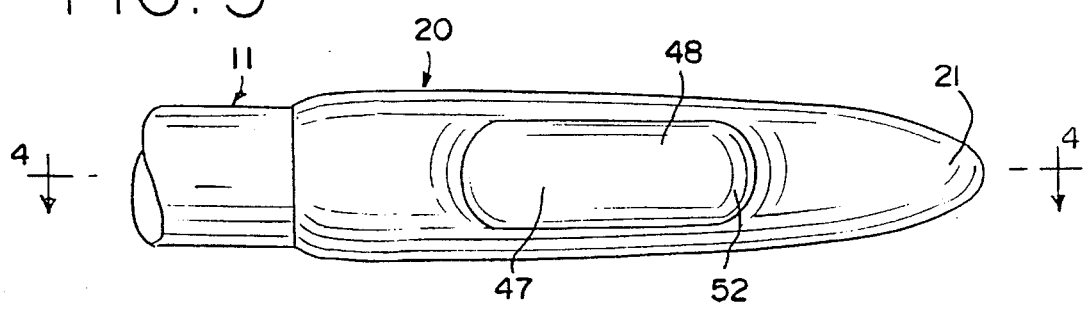
FIG. 3 is a top plan view of the bolus end of the catheter seen in FIG. 2.

As shown in FIGS. 2–4, the outer diameter of the bolus 20 decreases from the glue-area section 25 to the nose section 27. At the nose section 27, the outer diameter is equal to that of the tube 11. Accordingly, as shown in FIG. 3, the bolus 20 tapers inward slightly from the glue-area section 25 to the nose section 27. It should be recognized, however, that the tube 11 and the bolus 20 may be formed together as "one piece" through an insert injection molding process such that the bolus 20 is integrally formed with the tube 11 rather than the above-described construction. As a result of this molding process, the bolus 20 will have an outside diameter equal to that of the tube 11.

The cylindrical bore 31 has an inside diameter equal to the diameter of the outside surface of the tube 11. The terminal end 15 of the tube 11 is press fit into the bore 31 until it abuts the shoulder 33 and is glued in this position. In this relationship of the tube 11 to the body 21, the inner surface 37 of the tube passage is flush with a correspondingly shaped passage 41 in the flow passage section 26 of the body 21 or, more precisely, with the inner surface 42.

The passage 41 comprises two passage portions, a short axially extending portion 46 and a longer radial or base portion 47 which curves radially away from the axis of the body 21 and, through a side opening or port 48 in the body. The port 48 forms a single fluid ingress and egress point for the bolus 20 and the tube 11. As shown in FIG. 4, a septum segment 43 in the axial passage portion 46 mates with the septum 22 and extends into and terminates substantially at the end of the axial passage portion 46.

As best seen in FIGS. 4 and 6, the shape of the radial passage portion 47 determines the shape of the port 48. The port 48 is formed by removing a piece of the body 21 around greater than 180° of the circumference of the body 21. Preferably, the port 48 extends substantially around 190° of the circumference of the body 21. As a result, fluids delivered through the second lumen 24 pass around and over a large portion of the surface area of the nose section 27. Accordingly, the fluid passing over the bolus 20 is slowed down and the tendency of the bolus 20 for "whipping" is decreased.

Directly opposite the center of the port 48, the floor 52 of the radial passage portion 47 is built up progressively in the direction of the nose section 27 of the bolus body 21, so as to define a uniform arc terminating at the outer surface of the body 21. The radius of the arc of the floor 52 is relatively short. It must be at least as large as the inside diameter of the axial passage portion 46. However, it should be less than 5 times that diameter and is preferably between 2.5 and 3.75 times that diameter. In the 13 FR tube version shown in FIGS. 2–6, with an inside diameter of 0.130 inches, the radius of the floor 52 shown is 3.25 times 0.130 inches, or 0.426 inches, for example.

As shown in FIGS. 4 and 6, the aforedescribed formation of the port 48 by removal of a piece of the bolus body around greater than 180° of the circumference of the body leaves a bolus body segment 55 opposite the port, effectively connecting the bullet tip nose section 27 of the 55 forms a relatively short side wall 56 on each side of the flow passage section 26.

Turning to FIGS. 7–10, a modification of the bolus 20 embodying a second form of the invention is seen generally at 120. Corresponding reference numerals plus 100 digits are used to identify corresponding components. Here, the bolus 120 differs essentially in that the septum segment 143 terminates in the radial passage portion 147 of the bolus 120. Preferably, the septum segment 143 extends 0.175" past the end of the top wall 159 of the axial passage portion 146 into the radial passage portion 147. In addition, because the bolus body 121 has a length of 0.984" the body 120 is slightly longer than the form of FIGS. 1–6.

The port 148 has a slightly different configuration than the previous embodiment because the side walls 156 of the bolus 120 adjacent the opening for the first lumen 123 taper down sharply to the top surface 160 of the septum segment 143 and extend at this height to the distal end 162 of the septum segment. At the distal end 162 of the septum segment 143, the side walls 156 taper down to a height set by the lower surface 170 of the septum segment 143. Accordingly, the side walls 156 extend slightly lower adjacent the opening for the second lumen 124.

Turning to FIGS. 11–16, a modification of the bolus 20 embodying a third form of the invention is seen generally at 220. Corresponding reference numerals plus 200 digits are used to identify corresponding components. Here, bolus 220 differs from the bolus 20 essentially in that its body 221 has a first port 249 and second port 250 rather than a single port. The first port 249 is in fluid communication with the first lumen 223 and the second port 250 is in fluid communication with the second lumen 224. Both ports are substantially aligned and contained substantially within the top half of a traverse cross-section taken along the septum segment 243. As a result, both ports 249, 250 open from the same side of the bolus 220. In addition, because the bolus body 221 has a length of 1.100", the bolus 220 is slightly longer than the forms of FIGS. 1–10. Also, the glue-area section 225 tapers inward rather abruptly to the flow passage section 226 in contrast to the forms of FIGS. 1–10.

The first port 249 is smaller than the second port 250 and is formed through a side opening in the body 221 that extends upward from the top surface 260 of the septum segment 243. As a result, the first port 249 extends around 170° of the circumference of the body 221. The septum segment 243 extends into the radial passage portion 247 of the passage section 226 and has a divider element 262 that extends upward to further define the first port 249. As best seen FIGS. 12 and 13, the divider element 262 has an upper surface 264 that curves radially away from the axis of the body 221.

The second port 250 is formed from a similar side opening in the body 221 that extends upward from the lower surface 270 of the septum segment 243. As a result, the second port 250 extends around 190° of the circumference of the body 221. Accordingly, fluids exiting from the second lumen 224 pass around and over a large portion of the surface of the nose section 221 thereby reducing whipping of the bolus 220. It should recognized, however, that the flow rate of fluids exiting or entering the first port 249 and the second port 250 is relatively the same.

While preferred embodiments of the invention have been described, it should be understood that the invention is not so limited and modifications may be made without departing from the invention. For example, it should be recognized that the septum segment may be varied in length. In addition, the present invention could also be modified for use with a guide wire by incorporating a small hole through the end of the nose section. Accordingly, the stylet can pass through the lower lumen and then through the bolus. As a result, the scope of the invention is defined by the appended claims, and all devices that come within the meaning of the claims, either literally or by equivalence, are intended to be embraced therein.

We claim:

1. A multiple-lumen catheter for use in the delivery or the withdrawal and delivery of fluids to a patient, said catheter comprising:

a) an elongate generally cylindrical body having an axial passageway extending the length thereof;

b) a septum extending across the interior of the body and along the length thereof in order to divide the body into first and second lumens;

c) a bolus extending from a distal end of the body, the bolus having a tube connector section at one end, a nose section at the other end and a passage section between the connector section and the nose section, the nose section having a solid bullet-shaped construction; and d) the passage section containing an axial passage portion adjacent the connector section and a radial passage portion adjacent the nose section, the axial passage portion in fluid communication with the first and second lumens, the radial passage portion forming a single port through the side of the bolus and in fluid communication with the first and second lumens, the septum terminating in the axial passage portion of the bolus.

2. The multiple-lumen catheter of claim 1 further characterized in that:

a) the radial passage portion has an arcuate base below the port;

b) the arcuate base having a radius which is less than 5 times the inside diameter of the axial passage portion.

3. The multiple-lumen catheter of claim 2 further characterized in that:

a) the arcuate base has a radius which is between 2.75 and 3.75 times the inside diameter of the passage section.

4. The multiple-lumen catheter of claim 1 further characterized in that:

a) the body circumference tapers down from the connector section to the nose section.

5. A multiple-lumen catheter for use in the delivery or the delivery and withdrawal of fluids to a patient, said catheter comprising:

a) an elongate generally cylindrical body having an axial passageway extending the length thereof;

b) a septum extending across the interior of the body and the length thereof in order to divide the body into first and second lumens;

c) a bolus extending from a distal end of said body, the bolus having a tube connector section at one end, a nose section at the other end and a passage section between the connector section and the nose section;

d) the passage section containing an axial passage portion adjacent the connector section and a radial passage portion adjacent the nose section, the axial passage portion in fluid communication with the axial passageway of the body, the radial passage portion having a longitudinal cross-section along the septum forming a first portion and a second portion; and e) a first port and a second port located substantially within the first portion of the longitudinal cross-section of the radial passage section, the first port and the second port in fluid communication with the first and second lumens.

6. The multiple-lumen catheter of claim 5 further characterized in that:

a) the first and second lumens have a substantially D-shaped transverse cross-section.

7. The multiple-lumen catheter of claim 5 further characterized in that:

a) the bolus circumference tapers down from the connector section to the nose section.

8. The multiple-lumen catheter of claim 5 further characterized in that:

a) the radial passage section has an arcuate base below both the first and second ports;

b) the arcuate base having a radius which is less than 5 times the inside diameter of the axial passage section.

9. The multiple-lumen catheter of claim 8 further characterized in that:

a) the arcuate base has a radius which is between 2.75 and 3.75 times the inside diameter of the axial passage section.

10. The multiple-lumen catheter of claim 5 further characterized in that:

a) the septum terminates in the bolus prior to the nose section; and b) the nose section has a solid bullet-shaped construction.

11. The multiple-lumen catheter of claim 5 further characterized in that:

a) the body includes a radiopaque stripe.

12. A multiple-lumen catheter for use in the delivery or the delivery and withdrawal of fluids to a patient, said catheter comprising:

a) an elongate generally cylindrical body having an axial passageway extending the length thereof;

b) a septum extending across the interior of the body and the length thereof in order to divide the body into first and second lumens;

c) a bolus extending from a distal end of the body, the bolus having a tube connector section at one end, a nose section at the other end and a passage section between the connector section and the nose section;

d) the passage section containing an axial passage portion adjacent the connector section and a radial passage portion adjacent the nose section, the axial passage section in fluid communication the axial passageway of the body, the radial passage portion having a longitudinal cross-section along the septum forming a first portion and a second portion; and e) a first port and a second port located substantially within the first portion of the longitudinal cross-section of the radial passage portion, the septum extending into and terminating in the radial passage portion and having a divider element extending to an outer surface of the bolus in order to thereby form the first port and the second port, the first port and the second port in fluid communication with the first and second lumens respectively.

13. The multiple-lumen catheter of claim 12 further characterized in that:

a) the divider element has a generally curved top surface and a flat bottom surface.

14. The multiple-lumen catheter of claim 13 further characterized in that:

a) the radial passage portion includes side walls that extend upward to a top surface of the septum to form in part the first port, the side walls extending upward to a bottom surface of the septum to form in part the second port.

15. A multiple-lumen catheter for use in the delivery or the withdrawal and delivery of fluids to a patient, said catheter comprising:

a) an elongate generally cylindrical body having an axial passageway extending the length thereof;

b) a septum extending across the interior of the body and along the length thereof in order to divide the body into first and second lumens;

c) a bolus extending from a distal end of the body, the bolus having a tube connector section at one end, a nose section at the other end and a passage section between the connector section and the nose section; and d) the passage section containing an axial passage portion adjacent the connector section and a radial passage portion adjacent the nose section, the axial passage portion in fluid communication with the first and second lumens, the radial passage portion forming a single port through the side of the bolus and in fluid communication with the first and second lumens, the port extending around greater than 180° of the circumference of the body.

16. The multiple-lumen catheter of claim 15 further characterized in that:

a) the radial passage portion has an arcuate base below the port;

b) the arcuate base has a radius which is less than five times the inside diameter of the axial passage portion.

17. The multiple-lumen catheter of claim 16 further characterized in that:

a) the body circumference tapers down from the connector section to the nose section.

18. A multiple-lumen catheter for use in the delivery or the withdrawal and delivery of fluids to a patient, said catheter comprising:

a) an elongate generally cylindrical body having an axial passageway extending the length thereof;

b) a septum extending across the interior of the body and along the length thereof in order to divide the body into first and second lumens;

c) a bolus extending from a distal end of the body, the bolus having a tube connector section at one end, a nose section at the other end and a passage section between the connector section and the nose section; and d) the passage section containing an axial passage portion adjacent the connector section and a radial passage portion adjacent the nose section, the axial passage portion in fluid communication with the first and second lumens, the radial passage portion forming a single port through the side of the bolus and in fluid communication with the first and second lumens, the radial passage portion including side walls that extend upward to a top surface of the septum adjacent an opening for the first lumen, the side walls extending upward to a bottom surface of the septum adjacent an opening for the second lumen.

19. The multiple-lumen catheter of claim 18 further characterized in that:

a) the radial passage portion has an arcuate base below the port;

b) the arcuate base has a radius which is less than five times the inside diameter of the axial passage portion.

20. The multiple-lumen catheter of claim 19 further characterized in that:

a) the body circumference tapers down from the connector section to the nose section.

* * * * *